US00PP28999P2

(12) United States Plant Patent
Farrow

(10) Patent No.: US PP28,999 P2
(45) Date of Patent: Feb. 27, 2018

(54) ***SPIRAEA* PLANT NAMED 'CONSPIYET'**

(50) Latin Name: *Spiraea japonica*
Varietal Denomination: Conspiyet

(71) Applicant: The Conard-Pyle Company, West Grove, PA (US)

(72) Inventor: Michael W. Farrow, Warwick, MD (US)

(73) Assignee: The Conard-Pyle Company, West Grove, PA (US)

( * ) Notice: Subject to any disclaimer, the term of this patent is extended or adjusted under 35 U.S.C. 154(b) by 0 days.

(21) Appl. No.: 15/530,154

(22) Filed: Dec. 7, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Spiraea* plant named 'Conspiyet', characterized by its pure white-colored flowers, medium green-colored foliage, and moderately vigorous, compact, low-mounding growth habit, is disclosed.

1 Drawing Sheet

Latin name of genus and species of plant claimed: *Spiraea japonica.*

Variety denomination: 'Conspiyet'.

BACKGROUND OF THE INVENTION

The present invention relates to a new and distinct cultivar of *Spiraea* plant botanically known as *Spiraea japonica* and hereinafter referred to by the cultivar name 'Conspiyet'.

The new cultivar originated in a controlled breeding program in Earleville, Md. during spring 2011. The objective of the breeding program was the development of *Spiraea* cultivars having abundant inflorescences and compact growth habit.

The new *Spiraea* cultivar is the result of open-pollination. The female (seed) parent of the new cultivar is *Spiraea* 'Anthony Waterer', not patented, characterized by its rosy-pink colored flowers, medium green colored foliage, and low-spreading growth habit. The male (pollen) parent of the new cultivar is unknown. The new cultivar was discovered and selected as a single flowering plant within the progeny of the above stated open-pollination during August 2011 in a controlled environment in Earleville, Md.

Asexual reproduction of the new cultivar by terminal stem cuttings since August 2011 in West Grove, Pa. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Conspiyet' as a new and distinct cultivar of *Spiraea* plant:

1. Pure white-colored flowers;
2. Medium green-colored foliage; and
3. Moderately vigorous, compact, low-mounding growth habit.

Plants of the new cultivar differ from plants of the female parent primarily in having pure white flowers.

Of the many commercially available *Spiraea* cultivars, the most similar in comparison to the new cultivar is 'Shirobana', not patented. However, in side by side comparisons, plants of the new cultivar differ from plants of 'Shirobana' in at least the following characteristics:

1. Plants of the new cultivar maintain exclusively pure white flowers longer than plants of 'Shirobana'; and
2. Plants of the new cultivar have flowers that are more self-cleaning than plants of 'Shirobana'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Conspiyet'. The plants are 2 years old and were grown in a greenhouse in one-gallon containers in West Grove, Pa.

DETAILED BOTANICAL DESCRIPTION

Figure 1:
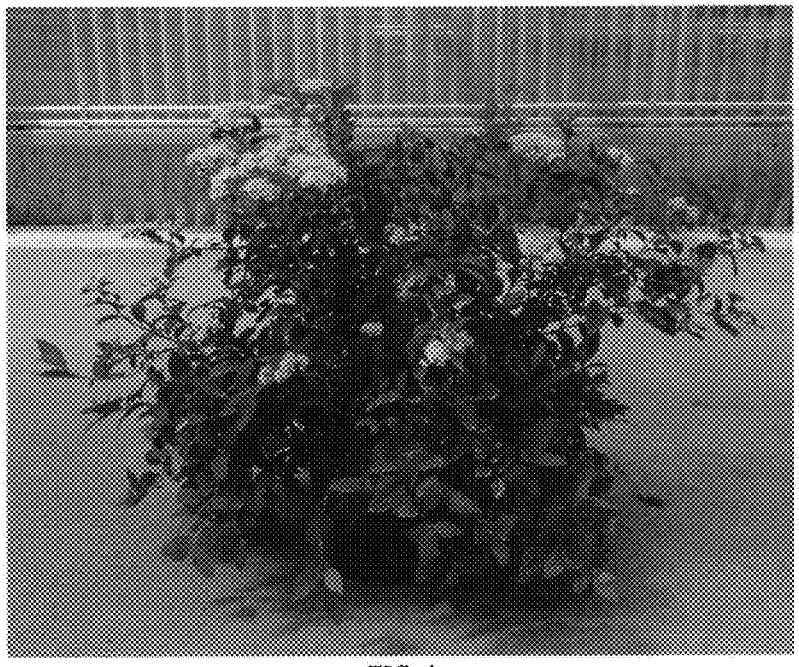
FIG. 1 illustrates a side view of the overall growth and flowering habit of 'Conspiyet'.
Figure 2:
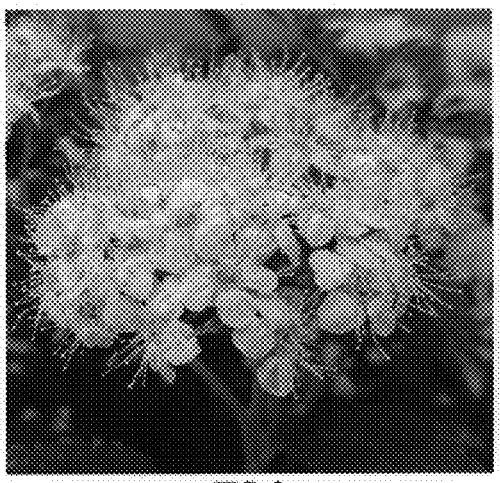
FIG. 2 illustrates a close-up view of a flower cluster of 'Conspiyet'.
Figure 3:
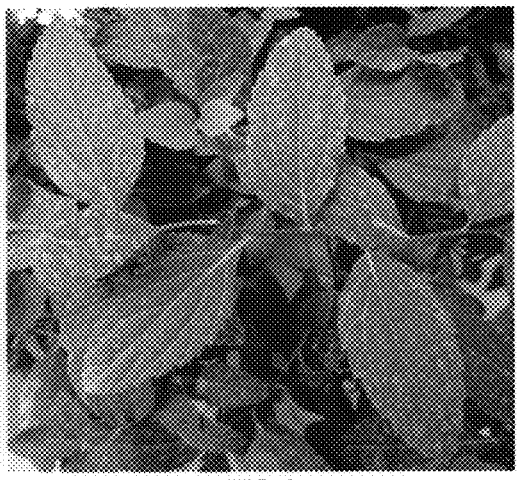
FIG. 3 illustrates a close-up view of the foliage of 'Conspiyet'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2016 under natural light conditions in West Grove, Pa.

The following descriptions and measurements describe two-year old plants produced from cuttings from stock plants and grown in one-gallon containers in a greenhouse in West Grove, Pa. Measurements and numerical values represent averages of typical plants.

Botanical classification: *Spiraea japonica* 'Conspiyet'.

Parentage:

*Female parent*.—*Spiraea×bumalda* 'Anthony Waterer', not patented.

*Male parent*.—Unknown.

Propagation:

*Type cutting*.—Terminal cuttings

*Time to initiate roots*.—Approximately 14 days.

*Time to produce a rooted cutting*.—Approximately 48 days.

*Root description*.—Fibrous and fine; white to brown in color.

*Rooting habit*.—Freely branching; dense.

Plant description:

*Commercial crop time*.—Approximately 15 weeks from a rooted cutting to finish in a 19.0 cm pot.

*Growth habit and general appearance*.—Moderately vigorous, compact, low-mounding growth habit.

*Hardiness*.—USDA Zone 4b (−20° F.).

*Heat tolerance*.—Regularly tolerates temperatures as high as 38.3° C. (101° F.) in the summer.

*Size*.—Height from soil level to top of plant plane: Approximately 37.0 cm. Width: Approximately 53.0 cm.

*Branching habit*.—Freely branching. Pinching not required. Apect: Erect to 45° from center. Quantity of branches per plant: Approximately 15 main stems per plant with approximately 10 lateral branches per stem.

*Lateral branches*.—Strength: Strong. Length: Approximately 18.3 cm. Diameter: Approximately 3.0 mm. Length of central internode: Approximately 10.0 mm. Texture of mature stem: Woody. Color of young stems: 145A. Color of mature stems: 200A.

Foliage description:

*General description*.—Form: Simple. Arrangement: Alternate. Fragrance: None detected.

*Leaves*.—Aspect: 45°. Shape: Ovate. Margin: Serrate. Apex: Acute. Base: Cuneate. Venation pattern: Pinnate. Length of mature leaf: Approximately 4.5 cm. Width of mature leaf: Approximately 2.5 cm. Texture of upper surface: Glabrous, moderately rugose. Texture of lower surface: Glabrous, ribbed. Color of upper surface of young foliage: 143B with venation color of 154B. Color of lower surface of young foliage: 143C with venation color of 143D. Color of upper surface of mature foliage: 136B with venation color of 151A. Color of lower surface of mature foliage: 136C with venation color of 151A.

*Petiole*.—Length: Approximately 4.0 mm. Diameter: Approximately 1.0 mm. Texture: Glabrous. Color of upper and lower surfaces: 151A.

Flowering description:

*Flowering season*.—Flowers in summer through early fall.

*Lastingness of individual inflorescence on the plant*.—Approximately 20 to 25 days.

*General description*.—Compound corymbs. Aspect: Facing upward to slightly outward. Fragrance: Slightly sweet. Quantity per plant: Approximately 30. Diameter: Approximately 8.0 cm to 11.0 cm. Height: Approximately 3.0 cm.

*Peduncle*.—Strength: Strong. Shape: Rounded. Aspect: Erect to about 45° from branch axis. Length: Approximately 1.0 cm. Diameter: Approximately 2.0 mm. Texture: Glabrous. Color: 59C.

Flower description:

*General description*.—Type: Single, rotate, not persistent. Aspect: Upright. Quantity per inflorescence: Approximately 150 to 180.

*Bud just before opening*.—Shape: Globose. Diameter: Approximately 2.0 mm. Color: NN155D.

*Corolla*.—Diameter: Approximately 7.0 mm. Depth: Approximately 3.0 mm.

*Petals*.—Quantity: 5, in a single whorl. Shape: Orbicular. Margin: Entire. Apex: Rounded. Base: Obtuse. Length: Approximately 3.0 mm. Width: Approximately 2.5 cm. Texture of upper and lower surfaces: Glabrous. Color of upper and lower surfaces when first and fully open: NN155D.

*Calyx*.—Shape: Star-shaped. Diameter: Approximately 5.0 mm. Depth: Approximately 3.0 mm.

*Sepals*.—Quantity: 5. Arrangement: in a single whorl. Shape: Lanceolate. Margin: Entire. Apex: Acute. Base: Fused. Texture of upper and lower surfaces: Glabrous. Color of upper surface when first and fully open: 135C. Color of lower surface when first and fully open: 137C.

*Pedicel*.—Strength: Strong. Aspect: Erect. Length: Approximately 5.0 mm. Diameter: Approximately 1.0 mm. Texture: Glabrous. Color: 143B.

*Reproductive organs*.—Androecium: Stamen quantity per flower: 35. Stamen length: Approximately 5.0 mm. Filament length: Approximately 5.0 mm. Filament color: NN155D. Anther shape: Globose. Anther length: Less than 1.0 mm. Anther color: 162B. Pollen amount: slight. Pollen color: 162B. Gynoecium: Syncarpous gynoecium with 5 styles fused to 1 ovary. Pistil length: Approximately 2.0 mm. Stigma shape: Garroted. Stigma color: NN155D. Style length: Approximately 1.5 mm. Style color: NN155D. Ovary length: Approximately 0.5 mm. Ovary color: N144C.

Seed and fruit production: Neither seed nor fruit production has been observed.

Disease and pest resistance: Resistance to pathogens and pests common to *Spiraea* has not been observed.

What is claimed is:

1. A new and distinct cultivar of *Spiraea* plant named 'Conspiyet', substantially as herein illustrated and described.

* * * * *